(12) United States Patent
Zheng et al.

(10) Patent No.: US 12,216,040 B2
(45) Date of Patent: *Feb. 4, 2025

(54) SAMPLE ANALYZER AND SAMPLE ANALYSIS METHOD

(71) Applicant: Shenzhen Mindray Bio-Medical Electronics Co., Ltd., Shenzhen (CN)

(72) Inventors: Wenbo Zheng, Shenzhen (CN); Bo Ye, Shenzhen (CN); Mingjin Guo, Shenzhen (CN); Chuanjian Wu, Shenzhen (CN); Huan Qi, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/715,841

(22) Filed: Apr. 7, 2022

(65) Prior Publication Data

US 2022/0334046 A1 Oct. 20, 2022

(30) Foreign Application Priority Data

Apr. 14, 2021 (CN) .......................... 202110402261.6

(51) Int. Cl.
| | |
|---|---|
| *G01N 15/1429* | (2024.01) |
| *G01N 15/01* | (2024.01) |
| *G01N 15/10* | (2024.01) |
| *G01N 15/1404* | (2024.01) |
| *G01N 15/1434* | (2024.01) |
| *G01N 33/50* | (2006.01) |

(52) U.S. Cl.
CPC ..... *G01N 15/1429* (2013.01); *G01N 15/1404* (2013.01); *G01N 15/1434* (2013.01); *G01N 33/5091* (2013.01); *G01N 33/5094* (2013.01); *G01N 2015/011* (2024.01); *G01N 2015/016* (2024.01); *G01N 2015/1006* (2013.01)

(58) Field of Classification Search
CPC .......... G01N 15/1429; G01N 15/1404; G01N 15/1434; G01N 33/5091; G01N 2015/1006; G01N 15/01; G01N 15/075; G01N 2015/1402; G01N 33/5094; G01N 15/1459; G01N 15/06; G01N 21/53; G01N 21/6486; G01N 2015/011; G01N 2015/016

See application file for complete search history.

(56) References Cited

U.S. PATENT DOCUMENTS

| 5,905,031 A * | 5/1999 | Kuylen | C12Q 1/34 435/29 |
|---|---|---|---|
| 7,916,280 B2 * | 3/2011 | Ueno | G01N 21/53 356/339 |
| 8,906,309 B2 * | 12/2014 | Krockenberger | G01N 15/1459 422/50 |
| 10,281,458 B2 * | 5/2019 | Masuda | G01N 33/4915 |
| 10,564,089 B2 * | 2/2020 | Gutierrez | G01N 15/12 |
| 10,883,916 B2 * | 1/2021 | Ye | G01N 15/14 |
| 2010/0248247 A1 * | 9/2010 | Kataoka | G01N 15/1459 435/6.1 |
| 2014/0051071 A1 * | 2/2014 | Yoshida | G01N 15/1459 435/6.1 |
| 2021/0041344 A1 * | 2/2021 | Ye | G01N 15/1429 |

FOREIGN PATENT DOCUMENTS

| WO | WO-2019206311 A1 * | 10/2019 | ......... G01N 15/1429 |

OTHER PUBLICATIONS

Machine generated translation of WO-2019206311-A1. Generated Feb. 2, 2024. Document originally published Oct. 31, 2019 (Year: 2019).*

* cited by examiner

*Primary Examiner* — Aaron J Kosar
*Assistant Examiner* — Andrew T Moehlman
(74) *Attorney, Agent, or Firm* — Kory D. Christensen

(57) ABSTRACT

Provided are a sample analyzer and a sample analysis method. The sample analyzer includes: a sampling apparatus configured to collect a blood sample; a sample preparation apparatus configured to mix the blood sample with a hemolytic agent and a dye to prepare a test sample liquid; an optical detection apparatus configured to detect side-scattered light signals and fluorescence signals generated by particles in the test sample liquid; and a processor configured to: generate a scatter diagram based on at least the side-scattered light signals and the fluorescence signals, and obtain a predetermined feature region, wherein an intensity of side-scattered light corresponding to a central position of the predetermined feature region is greater than an intensity of side-scattered light corresponding to a central position of a region containing neutrophil granulocyte population; and obtain a blast cell parameter based on the predetermined feature region.

15 Claims, 11 Drawing Sheets

SAMPLE ANALYZER AND SAMPLE ANALYSIS METHOD

CROSS-REFERENCE TO RELATED APPLICATIONS

This application claims priority to Chinese Patent Application No. 202110402261.6, entitled "SAMPLE ANALYZER AND SAMPLE ANALYSIS METHOD," and filed on Apr. 14, 2021, the contents of which are incorporated herein by reference.

TECHNICAL FIELD

The disclosure relates to blood analysis, and in particular, to a sample analyzer and a sample analysis method.

BACKGROUND

Cellular components of blood mainly include platelets, white blood cells, and red blood cells. The white blood cells further include lymphocytes, monocytes, neutrophil granulocytes, eosinophil granulocytes, and basophil granulocytes. These cells are generated in bone marrow, differentiate and mature from immature cells, and migrate to peripheral blood. Immature white blood cells, such as blast cells, do not appear in peripheral blood of a normal person, but appear in peripheral blood of patients with leukemia, marrow metastases of cancer cells and severe infectious diseases. Therefore, detecting blast cells in peripheral blood is of important reference significance for the diagnosis of leukemia.

SUMMARY

The following summary should not be interpreted as defining key features or necessary technical features of the claims and should not be used to determine the scope of protection of the claims.

One aspect of the disclosure provides a sample analyzer including:
- a sampling apparatus configured to collect a blood sample;
- a sample preparation apparatus provided with a reaction chamber and a reagent supply portion, where the reaction chamber is configured to receive the blood sample collected by the sampling apparatus, and the reagent supply portion is configured to supply a hemolytic agent and a dye to the reaction chamber, so that the blood sample collected by the sampling apparatus is mixed with the hemolytic agent and the dye provided by the reagent supply portion in the reaction chamber to prepare a test sample liquid;
- an optical detection apparatus including a light source, a flow chamber and an optical detector, wherein the light source is configured to emit a light beam to irradiate the flow chamber, the flow chamber is configured to communicate with the reaction chamber, wherein particles in the test sample liquid are capable of passing through the flow chamber one by one, and the optical detector is configured to detect scattered light signals and fluorescence signals generated by the particles passing through the flow chamber after the particles are irradiated by the light beam; and
- a processor, configured to perform the following steps: obtaining the scattered light signals and the fluorescence signals of the test sample liquid from the optical detection apparatus, wherein the scattered light signals include at least side-scattered light signals; generating a scatter diagram based on at least the side-scattered lights signal and the fluorescence signals, and obtaining a first predetermined feature region and a region containing neutrophil granulocytes population of the scatter diagram, wherein an intensity of side-scattered light corresponding to a central position of the first predetermined feature region is greater than an intensity of side-scattered light corresponding to a central position of the region containing neutrophil granulocytes population; and obtaining a blast cell parameter of the blood sample based on the first predetermined feature region.

In an embodiment, the processor is further configured to perform the following step: obtaining a region of lymphocyte population of the scatter diagram, wherein an intensity of fluorescence corresponding to the central position of the first predetermined feature region is greater than an intensity of fluorescence corresponding to a central position of the region of lymphocyte population.

In an embodiment, the region containing neutrophil granulocyte population is a region of white blood cell population, and the region of white blood cell population contains a region of lymphocyte population and a region of neutrophil granulocyte population, eosinophil granulocyte population and monocyte population.

In an embodiment, the region containing neutrophil granulocyte population is a region of neutrophil granulocyte population.

In an embodiment, the region containing neutrophil granulocyte population is a region of neutrophil granulocyte population, eosinophil granulocyte population and monocyte population.

In an embodiment, the blast cell parameter includes a particle concentration of blast cells, and the processor is further configured to perform the following step: generating alarm information when the particle concentration of the blast cells exceeds a first preset threshold.

In an embodiment, the blast cell parameter includes a ratio of a particle concentration of blast cells to a particle concentration of white blood cells in the blood sample, and the processor is further configured to generate alarm information when the ratio exceeds a second preset threshold.

In an embodiment, the processor is further configured to obtain the particle concentration of the white blood cells in the blood sample by at least one of the following manners: receiving the particle concentration of the white blood cells from external input; obtaining the particle concentration of the white blood cells using other detection channels; and obtaining the particle concentration of the white blood cells based on the scattered light signals and/or the fluorescence signals.

In an embodiment, the scattered light signals further include forward-scattered light signals, and the processor is further configured to perform the following step: obtaining a nucleated red blood cell parameter and/or a basophil granulocyte parameter of the blood sample based on the forward-scattered light signals and the fluorescence signals.

In an embodiment, obtaining a nucleated red blood cell parameter and/or a basophil granulocyte parameter of the blood sample based on the forward-scattered light signals and the fluorescence signals includes: generating a two-dimensional scatter diagram based on the forward-scattered light signals and the fluorescence signals, and obtaining the nucleated red blood cell parameter and/or the basophil granulocyte parameter based on the two-dimensional scatter diagram; or, generating a three-dimensional scatter diagram based on the forward-scattered light signals, the side-scattered light signals and the fluorescence signals, obtaining the nucleated red blood cell parameter and/or the basophil granulocyte parameter and the blast cell parameter according to the three-dimensional scatter diagram.

In an embodiment, the processor is further configured to perform the following steps: obtaining a second predetermined feature region of the scatter diagram, where an intensity of side-scattered light corresponding to a central position of the second predetermined feature region is greater than the intensity of side-scattered light corresponding to the central position of the region containing neutrophil granulocyte population, and an intensity of fluorescence corresponding to the central position of the second predetermined feature region is greater than the intensity of fluorescence corresponding to the central position of the region of lymphocyte population; and obtaining an immature granulocyte parameter of the blood sample based on the second predetermined feature region.

Another aspect of the disclosure provides a sample analyzer including:
- a sampling apparatus configured to collect a blood sample;
- a sample preparation apparatus provided with a reaction chamber and a reagent supply portion, wherein the reaction chamber is configured to receive the blood sample collected by the sampling apparatus, and the reagent supply portion is configured to supply a hemolytic agent and a dye to the reaction chamber, so that the blood sample collected by the sampling apparatus is mixed with the hemolytic agent and the dye provided by the reagent supply portion in the reaction chamber to prepare a test sample liquid, and wherein the hemolytic agent is used to lyse red blood cells, and the dye is used to stain organelles in blood cells;
- an optical detection apparatus including a light source, a flow chamber and an optical detector, wherein the light source is configured to emit a light beam to irradiate the flow chamber, the flow chamber is configured to communicate with the reaction chamber, wherein particles in the test sample liquid are capable of passing through the flow chamber one by one, and the optical detector is configured to detect, in a single test, scattered light signals and fluorescence signals generated by the particles passing through the flow chamber after the particles are irradiated by the light beam; and
- a processor, configured to perform the following steps: obtaining the scattered light signals and the fluorescence signals of the test sample liquid from the optical detection apparatus, wherein the scattered light signals include forward-scattered light signals and side-scattered light signals; obtaining a blast cell parameter of the blood sample based on the side-scattered light signals and the fluorescence signals; and obtaining a nucleated red blood cell parameter and/or a basophil granulocyte parameter of the blood sample based on the forward-scattered light signals and the fluorescence signals.

In an embodiment, obtaining a blast cell parameter of the blood sample based on the side-scattered light signals and the fluorescence signals includes: generating a scatter diagram based on the side-scattered light signals and the fluorescence signals; obtaining a predetermined feature region and a region containing neutrophil granulocyte population of the scatter diagram, wherein an intensity of side-scattered light corresponding to a central position of the predetermined feature region is greater than an intensity of side-scattered light corresponding to a central position of the region containing neutrophil granulocyte population; and obtaining the blast cell parameter of the blood sample based on the predetermined feature region.

In an embodiment, obtaining a blast cell parameter of the blood sample based on the side-scattered light signals and the fluorescence signals includes: generating a first two-dimensional scatter diagram based on the side-scattered light signals and the fluorescence signals, and obtaining the blast cell parameter based on the first two-dimensional scatter diagram; and obtaining a nucleated red blood cell parameter and/or a basophil granulocyte parameter of the blood sample based on the forward-scattered light signals and the fluorescence signals includes: generating a second two-dimensional scatter diagram based on the forward-scattered light signals and the fluorescence signals, and obtaining the nucleated red blood cell parameter and/or the basophil granulocyte parameter based on the second two-dimensional scatter diagram.

In an embodiment, obtaining a blast cell parameter of the blood sample based on the side-scattered light signals and the fluorescence signals; and obtaining a nucleated red blood cell parameter and/or a basophil granulocyte parameter of the blood sample based on the forward-scattered light signals and the fluorescence signals include: generating a three-dimensional scatter diagram based on the forward-scattered light signals, the side-scattered light signals and the fluorescence signals, obtaining the nucleated red blood cell parameter and/or the basophil granulocyte parameter and obtaining the blast cell parameter according to the three-dimensional scatter diagram.

Yet another aspect of the disclosure provides a sample analysis method including: obtaining a blood sample, and mixing the blood sample with a hemolytic agent and a dye to prepare a test sample liquid; detecting scattered light signals and fluorescence signals generated by particles in the test sample liquid after the particles are irradiated by light; obtaining the scattered light signals and the fluorescence signals of the test sample liquid, wherein the scattered light signals include at least side-scattered light signals; generating a scatter diagram based on at least the side-scattered light signals and the fluorescence signals, and obtaining a first predetermined feature region and a region containing neutrophil granulocyte population of the scatter diagram, wherein an intensity of side-scattered light corresponding to a central position of the first predetermined feature region is greater than an intensity of side-scattered light corresponding to a central position of the region containing neutrophil granulocyte population; and obtaining a blast cell parameter of the blood sample based on the first predetermined feature region.

In an embodiment, the method further includes: obtaining a region of lymphocyte population of the scatter diagram, wherein an intensity of fluorescence corresponding to the central position of the first predetermined feature region is greater than an intensity of fluorescence corresponding to a central position of the central position of the region of lymphocyte population.

In an embodiment, the blast cell parameter includes a particle concentration of blast cells, and the method further includes: generating alarm information when the particle concentration of the blast cells exceeds a first preset threshold.

In an embodiment, the blast cell parameter includes a ratio of a particle concentration of blast cells to a particle concentration of white blood cells in the blood sample, and the method further includes: generating alarm information when the ratio exceeds a second preset threshold.

Still another aspect of the disclosure provides a sample analysis method including: obtaining a blood sample, and mixing the blood sample with a hemolytic agent and a dye to prepare a test sample liquid, wherein the hemolytic agent is used to lyse red blood cells, and the dye is used to stain organelles in blood cells; detecting, in a single test, scattered light signals and fluorescence signals generated by particles in the test sample liquid after the particles are irradiated by light; obtaining the scattered light signals and the fluorescence signals of the test sample liquid, wherein the scattered light signals include at least forward-scattered light signals and side-scattered light signals; obtaining a blast cell parameter of the blood sample based on the side-scattered light signals and the fluorescence signals; and obtaining a nucleated red blood cell parameter and/or a basophil granulocyte parameter of the blood sample based on the forward-scattered light signals and the fluorescence signals.

In the sample analyzer and the sample analysis method according to embodiments of the disclosure, a scatter diagram is generated on the basis of side-scattered light signals and fluorescence signals, and a blast cell parameter of a blood sample can be accurately obtained by analyzing a first predetermined feature region of the scatter diagram.

BRIEF DESCRIPTION OF THE DRAWINGS

The above and other objectives, features and advantages of the disclosure will become more apparent from the description of embodiments of the disclosure in detail with reference to the accompanying drawings. The accompanying drawings, which are intended to provide further understanding of embodiments of the disclosure and constitute a part of the description, are intended to explain the disclosure together with the embodiments of the disclosure and not to limit the disclosure. In the accompanying drawings, same reference numerals generally indicate same components or steps.

DETAILED DESCRIPTION

Figure 1:
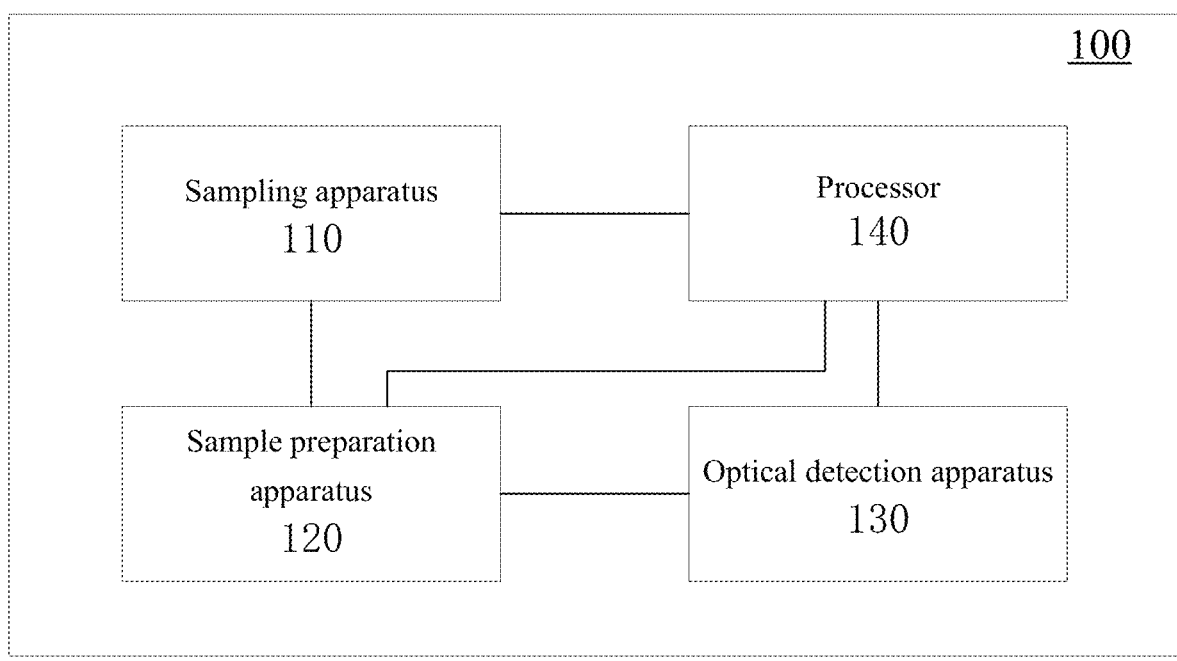
FIG. 1 is a structural block diagram of a sample analyzer according to an embodiment of the disclosure.

In order to clarity the objectives, technical solutions, and advantages of the disclosure, example embodiments will be described in detail below with reference to the accompanying drawings. The described embodiments are merely some rather than all of the embodiments of the disclosure. It should be understood that the example embodiments described herein do not constitute any limitation to the disclosure. All other embodiments derived by those skilled in the art without creative efforts on the basis of the embodiments of the disclosure described in the disclosure shall fall within the scope of the disclosure.

In the following description, many specific details are given to provide more thorough understanding of the disclosure. However, it is clear to those skilled in the art that the disclosure can be implemented without one or more of these details. In other examples, to avoid confusion with the disclosure, some technical features known in the art are not described.

It should be understood that the disclosure can be implemented in different forms and should not be construed as being limited to the embodiments presented herein. On the contrary, these embodiments are provided to achieve thorough and complete disclosure and fully pass the scope of the disclosure to those skilled in the art.

The terms used herein are only intended to describe the specific embodiments and do not constitute a limitation to the disclosure. As used herein, the singular forms of "a", "an", and "the/this" are also intended to include plural forms, unless the context clearly indicates otherwise. It should also be appreciated that the terms "composed of" and/or "including", when used in the description, determine the existence of described features, integers, steps, operations, elements, and/or components, but do not exclude the existence or addition of one or more other features, integers, steps, operations, elements, components, and/or groups thereof. As used herein, the term "and/or" includes any and all combinations of relevant listed items.

For thorough understanding of the disclosure, detailed structures will be provided in the following description to explain the technical solutions proposed by the disclosure. The optional embodiments of the disclosure are described in detail as follows. However, in addition to these detailed descriptions, the disclosure may further have other implementations.

A method for detecting a blast cell parameter includes: generating a first scatter diagram based on forward-scattered light signals and side-scattered light signals, and obtaining a first cell population in a predetermined region of the first scatter diagram; generating a second scatter diagram based on the forward-scattered light signals and fluorescence signals, and obtaining a second cell population in a predetermined region of the second scatter diagram, wherein cells belonging to both the first cell population and the second cell population are blast cells. This detection method requires detection of three kinds of optical signals, and a detection cost is high. In addition, when severe platelet (PLT) aggregation occurs, the forward-scattered lights may be very large due to the aggregation of a large number of PLTs, and the first cell population and the second cell population may contain some aggregated PLT cells, resulting in an inaccurate measurement result of the blast cell parameter.

To accurately measure the blast cell parameter, embodiments of the disclosure provide a sample analyzer and a sample analysis method, which are used to measure the blast cell parameter based on side-scattered light signals and forward-scattered light signals. Reference is made to FIG. 1 first for description of a sample analyzer according to an embodiment of the disclosure. FIG. 1 is a structural block diagram of a sample analyzer 100 according to an embodiment of the disclosure. As shown in FIG. 1, the sample analyzer 100 includes at least a sampling apparatus 110, a sample preparation apparatus 120, an optical detection apparatus 130, and a processor 140. Further, the sample analyzer 100 may further include a display apparatus, configured to display a sample analysis result obtained by the processor 140.

The sampling apparatus 110 is configured to collect a blood sample. For example, the sampling apparatus 110 is provided with a pipette (such as a sampling needle) with a pipette nozzle, and is provided with a driving portion. The driving portion is configured to drive the pipette to quantitatively aspirate a to-be-tested blood sample by using the pipette nozzle. For example, the sampling needle moves under the driving of the driving portion to aspirate a to-be-tested blood sample from a sample container containing the blood sample.

The sample preparation apparatus 120 is provided with at least one reaction chamber and a reagent supply portion, wherein the at least one reaction chamber is configured to receive the blood sample collected by the sampling apparatus, and the reagent supply portion is configured to supply a hemolytic agent and a dye to the reaction chamber, so that the blood sample collected by the sampling apparatus is mixed with the hemolytic agent and the dye provided by the reagent supply portion in the reaction chamber to prepare a test sample liquid.

For example, the hemolytic agent includes at least one surfactant selected from a cationic surfactant and a non-ionic surfactant. The hemolytic agent can slightly destroy cell membranes of white blood cells and blast cells and pores thus appear in cell membranes, which facilitates cell staining by using the dye. The white blood cells include basophil granulocytes, lymphocytes, and the like. Different cells have different cell characteristics, damage degrees of cell membranes of the cells are different, and quantities of dyes entering the cells are also different after actual treatment, and sizes of organelles of different cell types are different, therefore, for different types of white blood cells, dyes bound to cells are different, which makes different types of white blood cells produce different optical signals. The hemolytic agent can further dissolve and destroy red blood cells and platelets in the blood sample, and some incompletely destroyed red blood cells also form red blood cell ghosts, which has little influence on subsequent scattered light signals and fluorescence signals.

The dye in the embodiments of the disclosure can specifically bind to organelles in cells, and the binding of the dye to the organelles may also be referred to as staining. After the stained cells are irradiated by light with a certain wavelength, fluorescence signals of different levels will be generated according to the binding degree of the dye. Different kinds of cells have different cell structures and cell volumes, and in addition, cell sizes will be changed to varying degrees after reaction with a reagent, thereby producing scattered light signals of different sizes. Side-scattered light signals mainly reflect difference in morphology or complexity of cells, fluorescence signals mainly reflect difference in binding ability between different cells and a dye, and forward-scattered light signals mainly reflect different sizes of different cells.

The optical detection apparatus 130 is configured to detect the test sample liquid prepared by using the sample preparation apparatus 120 to obtain optical signals. In some embodiments, the optical detection apparatus 130 includes a light source, a flow chamber and an optical detector, wherein the light source is configured to emit a light beam to irradiate the flow chamber, the flow chamber is configured to communicate with the reaction chamber, wherein particles in the test sample liquid are capable of passing through the flow chamber one by one. The optical detector is configured to detect scattered light signals and fluorescence signals that are generated by the particles passing through the flow chamber after the particles are irradiated by the light beam. For example, the optical detection apparatus is provided with a light source, a beam shaping assembly and a flow chamber which are sequentially arranged in a straight line. A dichroscope is obliquely arranged on one side of the flow chamber. Part of lateral light emitted by cells in the flow chamber is transmitted through the dichroscope and is captured by a fluorescence detector arranged obliquely with respect to the dichroscope and behind the dichroscope, thereby obtaining fluorescence signals; and the other part of the lateral light is reflected by the dichroscope and is captured by a side-scattered light detector arranged obliquely with respect to the dichroscope and in front of the dichroscope, thereby obtaining side-scattered light signals. Optionally, the optical detection apparatus further includes a forward light detector which is arranged in a straight line with the light source, the beam shaping assembly and the flow chamber and is configured to capture forward-scattered light signals.

The processor 140 is configured to perform the following steps: obtaining the scattered light signals and the fluorescence signals of the test sample liquid from the optical detection apparatus 130, wherein the scattered light signals include at least side-scattered light signals; generating a scatter diagram based on at least the side-scattered light signals and the fluorescence signals, and obtaining a first predetermined feature region and a region containing neutrophil granulocyte (NEU) population of the scatter diagram, wherein an intensity of side-scattered light corresponding to a central position of the first predetermined feature region is greater than an intensity of side-scattered light corresponding to a central position of the region containing neutrophil granulocyte population; and obtaining a blast cell (Blast) parameter of the blood sample based on the first predetermined feature region. Further, the processor 140 is further configured to control the display apparatus to display the blast cell parameter obtained by the processor.

In some embodiments, the processor 140 includes at least a processing assembly, an RAM, an ROM, a communication interface, a memory, and an I/O interface. The processing assembly, the RAM, the ROM, the communication interface, the memory and the I/O interface communicate by using a bus. The processing assembly may be a CPU, a GPU or other chips with a computing capability. The memory contains various computer programs, such as an operating system and an application program, which are executed by the processor assembly, and data required for the execution of the computer programs. In addition, in the process of sample analysis, any data that needs to be stored locally may be stored in the memory. The I/O interface includes a serial interface such as a USB, IEEE1394 or RS-232C, a parallel interface such as an SCSI, IDE or IEEE1284, and an analog signal interface composed of a D/A converter, A/D converter, and the like. The I/O interface is connected to an input device, such as a keyboard, a mouse, a touch screen or other control buttons, and a user can directly input data to the processor 140 by using the input device. In addition, the I/O interface may be further connected to a display apparatus with a display function, such as: a liquid crystal display, a touch screen, or an LED display screen. The processor 140 may output processed data as image display data to the display apparatus for display, such as: sample analysis data and an instrument operating parameter. The communication interface may be an interface which supports any currently known communication protocol. The communication interface communicates with the outside world over a network. The processor 140 may transmit, by using a certain communication protocol through the communication interface, data with any apparatus connected over the network.

The processor 140 receives the side-scattered light signals and the fluorescence signals which are output by the optical detection apparatus 130, uses the side-scattered light signal and the fluorescence signal of each particle as a feature data set representing said particle, and analyzes the blood sample by analyzing and processing the particle feature data. Specifically, the processor 140 generates a required scatter diagram according to the feature data set of each particle, and detects the blast cell parameter according to the scatter diagram. For example, the processor 140 may count blast cell particles in the predetermined feature region, so as to obtain a particle concentration of blast cells.

The scatter diagram refers to a collection composed of feature data sets of each cell particle. The scatter diagram may be a two-dimensional scatter diagram or a three-dimensional scatter diagram drawn by combining with forward-scattered light. Cells mapped to the scatter diagram are referred to as particles, and cells of a same type are in aggregated distribution in the scatter diagram because of their similar optical signal characteristics, and are referred to as a particle population. The scatter diagram may be presented not in graphic form, but in the form of a data array (such as a two-dimensional data array) of optical signal values or the like. Hereinafter, the scatter diagram in graphic form will be described as an example. FIGS. 2 to 5 exemplarily show two-dimensional scatter diagrams generated by the processor 140 according to fluorescence intensity information and side-scattered light intensity information of each cell.

The applicant has found through research that a first predetermined feature region exists in the scatter diagram generated according to the side-scattered light signals and the fluorescence signals, and if blast cells exist in the blood sample, a particle population of the blast cells stably appears in the first predetermined feature region. An intensity of side-scattered light corresponding to a central position of the first predetermined feature region is greater than an intensity of side-scattered light corresponding to a central position of the region containing neutrophil granulocyte population, which may because: when the blood sample reacts with the hemolytic agent and the dye, the hemolytic agent mainly destroys cytoplasm of blast cells and keeps an original state of organelles. The dyes used in the embodiment of the disclosure is mainly used to stain organelles. Because blast cells are relatively immature cells, a proportion of organelles in the blast cells is greater than that of organelles in neutrophil granulocytes, so that an intensity of side-scattered light signals generated by the blast cells is greater than that of side-scattered light signals generated by the neutrophil granulocytes.

Since the position of the region containing neutrophil granulocyte population is relatively stable, the position of the first predetermined feature region is described with the region containing neutrophil granulocyte population as a reference in the embodiment of the disclosure. In an embodiment, the region containing neutrophil granulocyte population may be a separate region of neutrophil granulocyte population, and the processor 140 may obtain a neutrophil granulocyte parameter of the blood sample based on this region.

Optionally, the region containing neutrophil granulocyte population may also contain other cell populations besides the neutrophil granulocyte population. In an embodiment, the region containing neutrophil granulocyte population may be a region of white blood cell (WBC) population, wherein the white blood cell population region refers to a region of normal white blood cell population. Specifically, the region of white blood cell population contains a region of lymphocyte (LYM) population and a region of neutrophil granulocyte population, eosinophil granulocyte (EOS) population and monocyte (MON) population. In another embodiment, the region containing neutrophil granulocyte population is a region of neutrophil granulocyte population, eosinophil granulocyte population and monocyte population, but does not contain a region of lymphocyte population. The region containing neutrophil granulocyte population shown in FIGS. 2 to 5 is a region of neutrophil granulocyte population, eosinophil granulocyte population and monocyte population.

Figure 2:
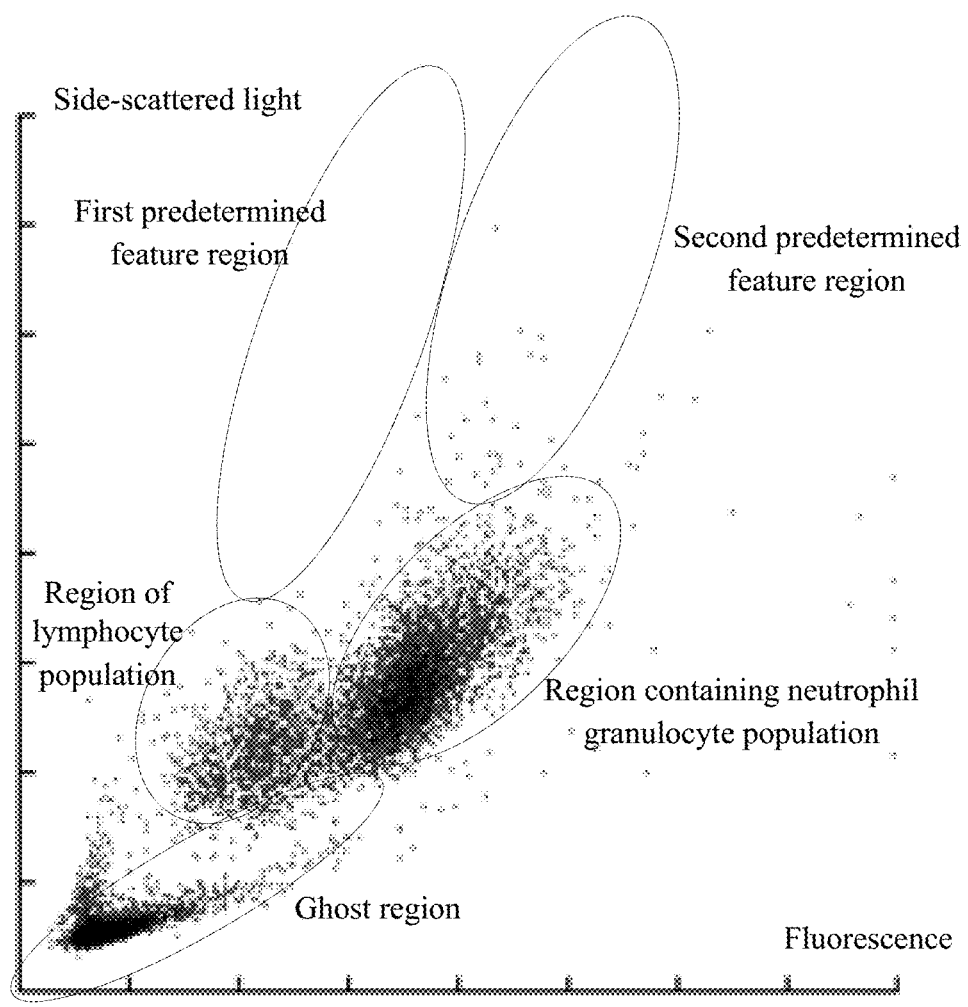
FIG. 2 is a two-dimensional scatter diagram of a blood sample containing blast cells according to an embodiment of the disclosure.
Figure 3:
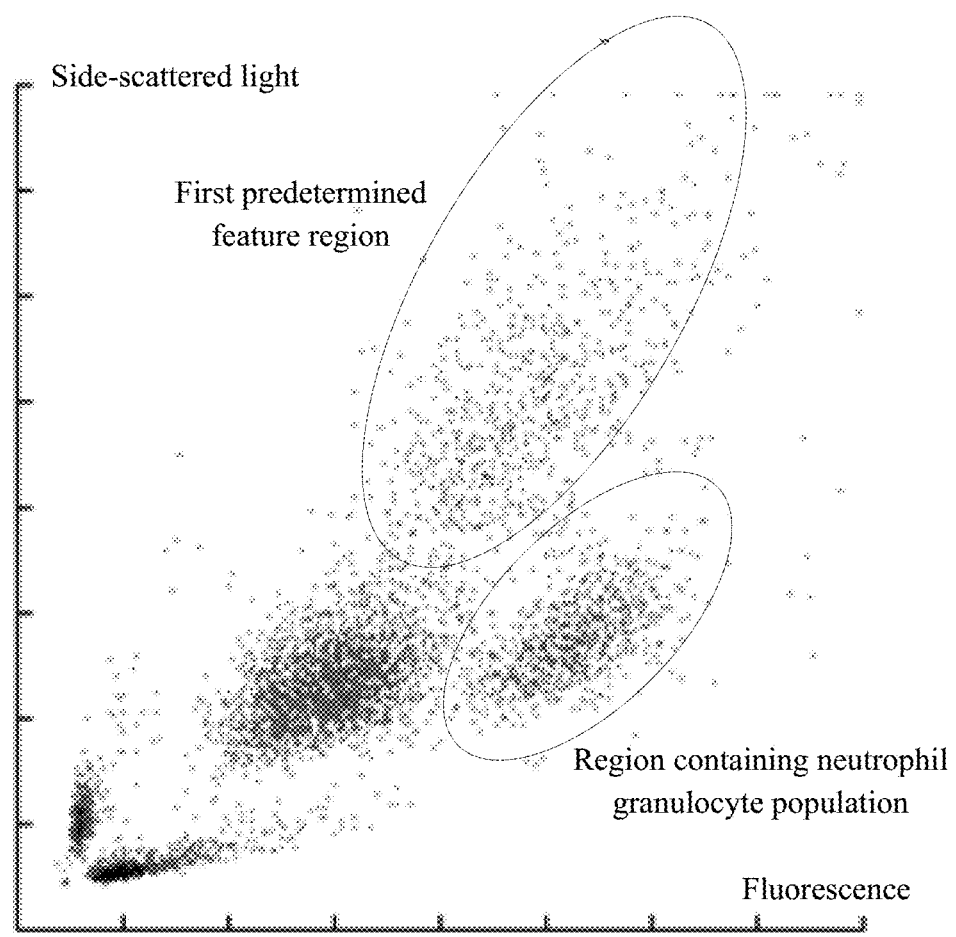
FIG. 3 is a two-dimensional scatter diagram of a normal blood sample according to an embodiment of the disclosure.

Referring to FIG. 2 and FIG. 3, in the fluorescence-side-scattered light scatter diagram, the first predetermined feature region is located above the region containing neutrophil granulocyte population. It may be understood that the scatter diagram generated according to the fluorescence signals and side-scattered light signals may also be a side-scattered light-fluorescence scatter diagram, in which the first predetermined feature region is located on the right side of the region containing neutrophil granulocyte population. The first predetermined feature region may be oval, circular, rectangular or in another suitable shape.

In the examples shown in FIG. 2 and FIG. 3, an intensity of fluorescence corresponding to a central position of the first predetermined feature region is less than an intensity of fluorescence corresponding to a central position of the region containing neutrophil granulocyte population. However, in other embodiments, if the reagent or illumination condition or the like changes, the intensity of fluorescence corresponding to the central position of the first predetermined feature region may also be greater than the intensity of fluorescence corresponding to the central position of the region containing neutrophil granulocyte population.

In an embodiment, the position and size of the first predetermined feature region may be fixed, that is, the fluorescence signal intensity and the side-scattered light signal intensity corresponding to the region are predetermined. In some embodiments, fluorescence signals and side-scattered light signals of a normal blood sample without blast cells and an abnormal blood sample with blast cells may be measured respectively in the same detection system, and scatter diagrams are generated. By comparing the scatter diagrams of the two, a certain region is found above the region containing neutrophil granulocyte population (taking fluorescence-side-scattered light scatter diagram as an example), and a particle population appears in this region of the abnormal blood sample, but no particle population appears in this region of the normal blood sample, so that the region is determined as the predetermined feature region.

In another embodiment, the position and size of the first predetermined feature region may also be floating, for example, the position of the first predetermined feature region may be dynamically adjusted according to certain rules with respect to the position of the region containing neutrophil granulocyte population in the scatter diagram. In this embodiment, after generating the scatter diagram, the processor 140 further needs to determine the first predetermined feature region in the scatter diagram according to at least the region containing neutrophil granulocyte population, and then obtain the blast cell parameter according to the first predetermined feature region. For example, in addition to the region containing neutrophil granulocyte population, the processor 140 may determine the position and size of the first predetermined feature region according to a region of other cell population in the scatter diagram.

In some embodiments, the processor 140 is further configured to obtain a region of lymphocyte population in the scatter diagram, wherein an intensity of fluorescence corresponding to the central position of the first predetermined feature region is greater than an intensity of fluorescence corresponding to a central position of the region of lymphocyte population. The processor 140 may determine the position of the first predetermined feature region according to both the region of lymphocyte population and the region containing neutrophil granulocyte population. With continued reference to FIG. 2, in the fluorescence-side-scattered light scatter diagram, the region of lymphocyte population is located on the left side of the first predetermined feature region. In the example shown in FIG. 2, the intensity of side-scattered light corresponding to the central position of the first predetermined feature region is greater than an intensity of side-scattered light corresponding to a central position of the region of lymphocyte population. In other embodiments, the intensity of side-scattered light corresponding to the central position of the first predetermined feature region may also be less than the intensity of side-scattered light corresponding to the central position of the region of lymphocyte population.

With continued reference to FIG. 2 and FIG. 3, FIG. 2 is a fluorescence-side-scattered light scatter diagram of a blood sample containing blast cells, and FIG. 3 is a fluorescence-side-scattered light scatter diagram of a normal blood sample. Comparing FIG. 2 with FIG. 3, with regard to the normal blood sample, no particle population appears in the first predetermined feature region, while with regard to the blood sample containing blast cells, a particle population of blast cells appears in the first predetermined feature region. Therefore, it can be seen that the blast cell parameter can be obtained by analyzing scattered points in the first predetermined feature region.

Figure 4:
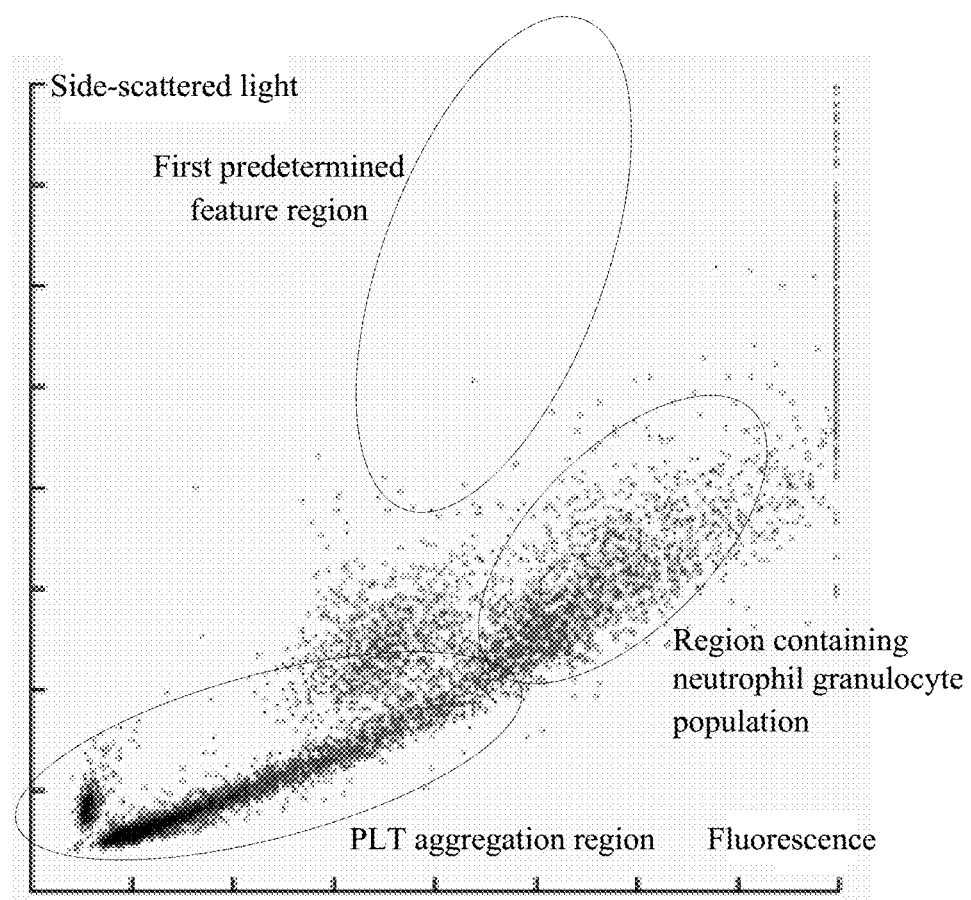
FIG. 4 is a two-dimensional scatter diagram of a blood sample in which PLT aggregation occurs according to an embodiment of the disclosure.
Figure 5:
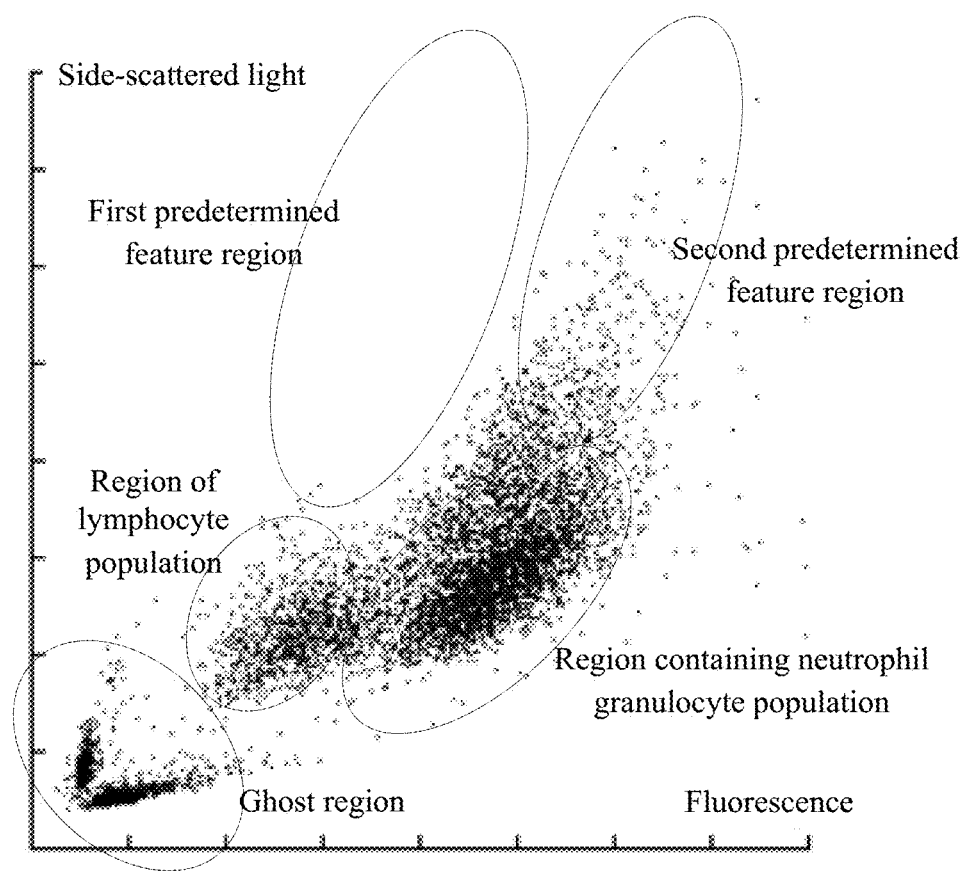
FIG. 5 is a two-dimensional scatter diagram of a blood sample with a high immature granulocyte percentage according to an embodiment of the disclosure.

Further, referring to FIG. 4, FIG. 4 is a fluorescence-side-scattered light scatter diagram of a blood sample in which PLT aggregation occurs. As can be seen from FIG. 4, because in the embodiments of the disclosure, the blast cell parameter is obtained according to the scatter diagram generated from the fluorescence signals and the side-scattered light signals, there is no overlap between the PLT aggregation region and the first predetermined feature region, so that the PLT aggregation does not affect the measurement result of the blast cell parameter.

Since blast cells do not appear in a normal peripheral blood sample, in a further embodiment, the processor 140 may further determine whether to generate alarm information on positive blast cells according to the detected blast cell parameter. The alarm information includes but is not limited to alarm information in form of text, sound, light, a pop-up window, or the like.

In an embodiment, the processor 140 may determine whether to generate alarm information based on a particle concentration of blast cells. Specifically, the processor 140 is configured to perform the following step: generating alarm information when the particle concentration of the blast cells exceeds a first preset threshold. The first preset threshold may be an empirical value obtained according to experimental statistics, but it is understandable that the first preset threshold may be adjusted according to an actual situation.

In another embodiment, the processor 140 may further determine whether to generate alarm information based on a ratio of a particle concentration of blast cells to a particle concentration of white blood cells in the blood sample. Specifically, the processor 140 is configured to perform the following step: generating alarm information when the ratio of the particle concentration of the blast cells to the particle concentration of the white blood cells exceeds a second preset threshold. The second preset threshold may be an empirical value obtained according to experimental statistics, or may be adjusted according to an actual situation.

The particle concentration of the white blood cells is the particle concentration of the white blood cells of the same blood sample used to detect the blast cell parameter. The processor 140 may receive the particle concentration of the white blood cells input from outside, or may obtain the particle concentration of white blood cells using other detection channels of the sample analyzer. The other detection channels include but are not limited to a white blood cell classification channel (DIFF). The processor 140 may further obtain the particle concentration of the blast cell parameter and the particle concentration of the white blood cell parameter through a same detection channel, that is, after obtaining the scattered light signals and the fluorescence signals, the processor may generate a scatter diagram according to the scattered light signals and the fluorescence signals, and obtain a particle concentration of white blood cells according to the scatter diagram, and the same detection channel may be a WNB (white blood cells, basophil granulocytes and nucleated red blood cells) channel.

Referring to FIG. 4, in the embodiments of the disclosure, although no PLT particle population exists in the first predetermined feature region, the detection result of the blast cell parameter will not be affected, but the PLT particle population may affect the detection result of the white blood cell parameter. PLTs are a part of ghost, and the ghost is of a cell fragment structure formed by cell membrane rupture caused by low permeability or reagent treatment of cells such as red blood cells or platelets in the blood sample. PLT aggregation may occur in some samples, which will interfere with the detection of white blood cells. Therefore, when calculating the ratio of the particle concentration of blast cells to the particle concentration of white blood cells in a blood sample, if the processor 140 obtains the particle concentration of the white blood cells based on the same detection channel or other detection channels, it is required to remove the interference caused by PLT aggregation to the measurement of the white blood cell parameter.

It has been found through research that a particle would generate a pulse when passing through a detection region, and the width of the pulse (referred to as pulse width for short) can reflect the time during which the particle passes through the detection region, and thus can represent the size of the particle. When the flow rate is constant, the smaller the particle is, the shorter the time during which the particle passes through the detection region is, and in turn the smaller the corresponding pulse width will be; whereas the larger the particle is, the longer the time during which the particle passes through the detection region is, and in turn the greater the corresponding pulse width will be. In a sample where platelet aggregation occurs, the width of the pulse generated by an aggregated particle when passing through the detection region is relatively large. Theoretically, aggregated platelet particles and white blood cells can be distinguished by using the size of the pulse width. However, due to a different number of aggregated platelets, the distribution range of the particle size of the platelet population is relatively wide, and some aggregated platelet particles with a larger size overlap with white blood cell population, so it is difficult to well distinguish white blood cells from aggregated platelet particles only by using pulse width. Therefore, in embodiments of the disclosure, according to the difference in pulse width between interfering particles and white blood cell particles, a new reinforcement signal is formed by using a functional combination of an optical signal and a pulse width signal, and white blood cell particles are distinguished from platelet particles by using a relatively large difference in the reinforcement signal between the white blood cell particles and the platelet particles.

Specifically, a pulse width of at least one optical signal is obtained first, and a reinforcement signal is obtained according to the pulse width of the at least one optical signal and a combined optical signal. The combined optical signal may be selected from any kind of optical signals. The combined calculation increases the difference in the reinforcement signal between white blood cell particles and interfering particles relative to the difference between the two in the combined optical signal. The optical signal of which the pulse width undergoing statistics and the combined optical signal may be the same optical signal or may be different optical signals. Then, a new scatter diagram is formed on the basis of the reinforcement signal and other signals, and the other signals may be at least one optical signal different from the combined optical signal, or may be other reinforcement signals. The white blood cell particles and the interfering particles are distinguished from each other according to the new scatter diagram. Because the reinforcement signal increases the difference in the reinforcement signal between the white blood cell particles and the interfering particles relative to the difference between the two in the combined optical signal, the white blood cell particles can be distinguished from the interfering particles on the scatter diagram based at least on the reinforcement signal.

For example, a reinforcement signal may be obtained according to a fluorescence signal and a pulse width signal, and a new scatter diagram is generated on the basis of the reinforcement signal and a forward-scattered light signal or a side-scattered light signal, so as to distinguish white blood cell particles from aggregated platelet particles. The pulse width signal may be any one of a fluorescence signal, a forward-scattered light signal and a side-scattered light signal.

Alternatively, a reinforcement signal may be obtained according to a forward-scattered light signal and a pulse width signal, and a new scatter diagram is generated on the basis of the reinforcement signal and a side-scattered light signal or a fluorescence signal, so as to distinguish white blood cell particles from aggregated platelet particles. The pulse width signal may be any one of a fluorescence signal, a forward-scattered light signal and a side-scattered light signal.

Alternatively, a reinforcement signal may be obtained according to a side-scattered light signal and a pulse width signal, and a new scatter diagram is generated on the basis of the reinforcement signal and a forward-scattered light signal or a fluorescence signal, so as to distinguish white blood cell particles from aggregated platelet particles. The pulse width signal may be any one of a fluorescence signal, a forward-scattered light signal and a side-scattered light signal.

After obtaining the particle concentration of the white blood cells and the particle concentration of the blast cells, the processor 140 calculates a ratio of the particle concentration of the blast cells to the particle concentration of the white blood cells. For example, the particle concentration of the white blood cells is denoted as WBC_Count, and the particle concentration of the blast cells is denoted as Blast_Count, then the percentage of the particle concentration of the blast cells in the particle concentration of the white blood cells, Blast %, is:

$$\text{Blast\%} = \frac{\text{Blast\_Count}}{\text{WBC\_Count}} \times 100\%;$$

and the processor 140 generates alarm information when Blast % exceeds a second preset threshold.

In addition to the blast cell parameter, the sample analyzer 100 according to the embodiments of the disclosure may further detect parameters of other cells. Further, the sample analyzer 100 according to the embodiments of the disclosure may obtain the blast cell parameter and parameters of other cells in a single test through the same detection channel. In an embodiment, the processor 140 may obtain forward-scattered light signals collected by the optical detection apparatus 130, and obtain a nucleated red blood cell (NRBC) parameter or a basophil granulocyte (BASO) parameter of the blood sample on the basis of the forward-scattered light signals and the fluorescence signals, or obtain both the nucleated red blood cell parameter and the basophil granulocyte parameter on the basis of the forward-scattered light signals and the fluorescence signals. Nucleated red blood cells are immature red blood cells, and exist in bone marrow under normal circumstances. No nucleated red blood cells appear in a peripheral blood sample of a normal person. Nucleated red blood cells appear in a blood sample because immature bone marrow erythroid cells are released into the blood sample. Thus, detecting both the nucleated red blood cell parameter and the blast cell parameter is beneficial to comprehensive analysis of the two.

Figure 6:
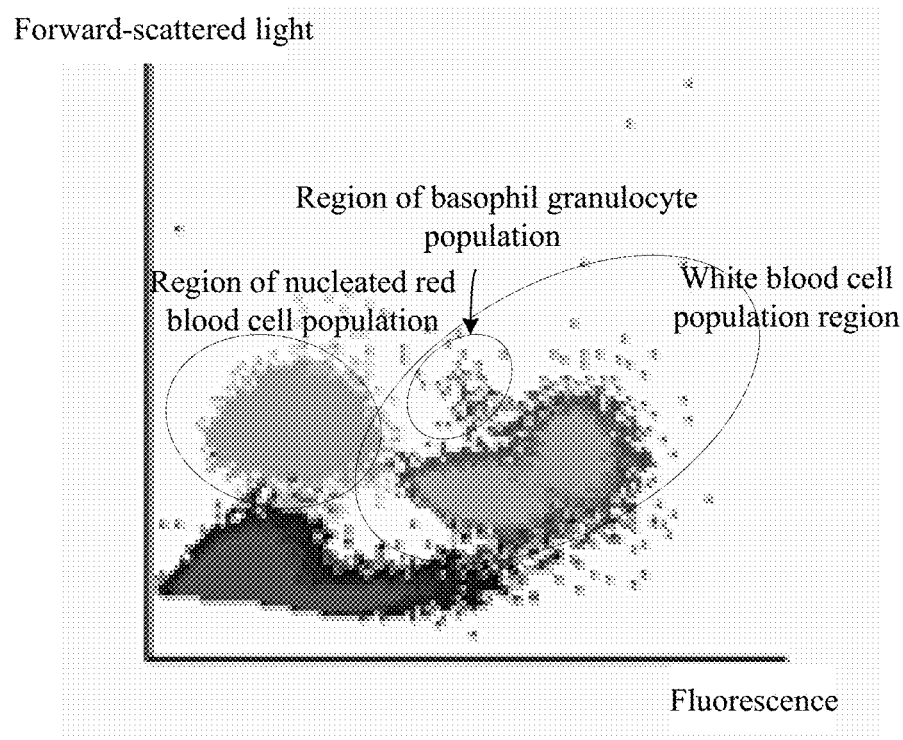
FIG. 6 is a two-dimensional scatter diagram generated on the basis of forward-scattered light signals and fluorescence signals according to an embodiment of the disclosure.

For example, as shown in FIG. 6, the processor 140 may generate a two-dimensional scatter diagram based on the forward-scattered light signals and the fluorescence signals, and obtain the nucleated red blood cell parameter and the basophil granulocyte parameter based on the two-dimensional scatter diagram. Specifically, the processor 140 may obtain the nucleated red blood cell parameter of the blood sample based on a region of nucleated red blood cell population in the two-dimensional scatter diagram, and obtain the basophil granulocyte parameter of the blood sample based on a region of basophil granulocyte population in the two-dimensional scatter diagram. The region of basophil granulocyte population is located inside the region of white blood cell population. Bare nucleuses formed by treating nucleated red blood cells with a reagent undergo pyknosis, and bind with a fluorescent dye with a relatively small mount, and the fluorescence signals are relatively low. Therefore, an intensity of fluorescence corresponding to a central position of the region of nucleated red blood cell population is less than an intensity of fluorescence corresponding to a central position of the region of white blood cell population.

Figure 7:
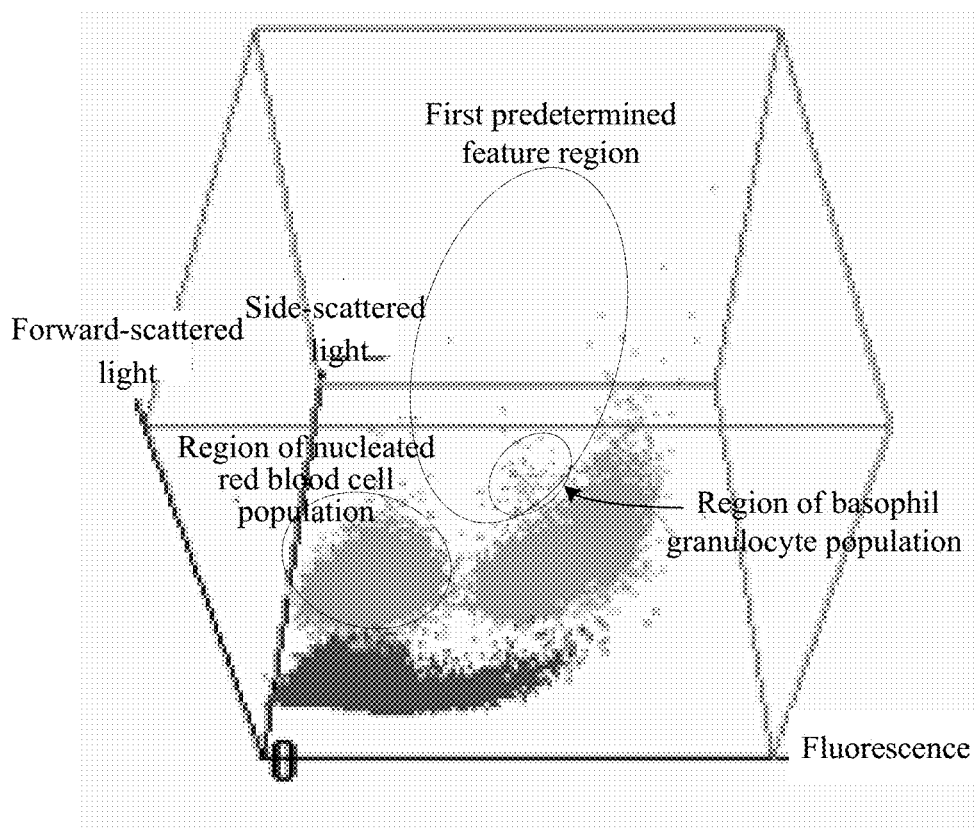
FIG. 7 is a three-dimensional scatter diagram generated on the basis of forward-scattered light signals, side-scattered light signals and fluorescence signals according to an embodiment of the disclosure.

Alternatively, the processor 140 may generate a three-dimensional scatter diagram based on the forward-scattered light signals, the side-scattered light signals and the fluorescence signals, and obtain the nucleated red blood cell parameter, the basophil granulocyte parameter and the blast cell parameter according to the three-dimensional scatter diagram. Referring to FIG. 7, the processor 140 may obtain a nucleated red blood cell parameter of a blood sample based on a region of nucleated red blood cell population in the three-dimensional scatter diagram, obtain a basophil granulocyte parameter of the blood sample based on a region of basophil granulocyte population in the three-dimensional scatter diagram, and obtain a blast cell parameter of the blood sample based on the first predetermined feature region in the three-dimensional scatter diagram.

In some embodiments, the processor 140 may further obtain an immature granulocyte parameter of the blood sample in the same test while obtaining the blast cell parameter. Immature granulocytes are also immature white blood cells, and detecting the immature granulocyte parameter and the blast cell parameter is beneficial to comprehensive analysis of the two. Specifically, the processor 140 is configured to obtain a second predetermined feature region of the scatter diagram, and obtain the immature granulocyte parameter of the blood sample based on the second predetermined feature region. Referring to FIG. 2, an intensity of side-scattered light corresponding to a central position of the second predetermined feature region is greater than the intensity of side-scattered light corresponding to the central position of the region containing neutrophil granulocyte population, and an intensity of fluorescence corresponding to the central position of the second predetermined feature region is greater than the intensity of fluorescence corresponding to the central position of the region of lymphocyte population.

Similarly, the position and size of the second predetermined feature region may be fixed, that is, the fluorescence signal intensity and the side-scattered light signal intensity corresponding to the region are predetermined. Alternatively, the position and size of the second predetermined feature region may also be floating, for example, the position of the second predetermined feature region may be dynamically adjusted according to certain rules with respect to the position of the region containing neutrophil granulocyte population and the position of the region of lymphocyte population in the scatter diagram.

In some embodiments, the processor 140 may further generate alarm information when the particle concentration of immature granulocytes exceeds a third preset threshold, or generate alarm information when a ratio of the particle concentration of immature granulocytes to the particle concentration of white blood cells exceeds a fourth preset threshold.

To further confirm the detection effect of the blast cell parameter using the sample analyzer provided by the embodiments of the disclosure, more than 50 blood samples were randomly selected and tested as follows:

1. Each blood sample was tested by the sample analyzer according to the embodiments of the disclosure, and the ratio (Blast %) of the particle concentration of blast cells to the particle concentration of white blood cells in each blood sample was obtained;
2. Blast cells were manually microscopically examined under a microscope, the blood samples were analyzed one by one, at least 100 white blood cells were manually counted, the number of white blood cells was recorded as WBC_Total_Manual, the number of blast cells in all counted white blood cells of each blood sample was obtained and recorded as Blast_num_Manual, and then a reference value of the proportion of blast cells (that is, the ratio of the particle number of blast cells to the particle number of white blood cells) was obtained and recorded as Blast %_Manual, where $$\text{Blast\%\_Manual} = \frac{\text{Blast\_num\_Manual}}{\text{WBC\_Total\_Manual}} \times 100\%.$$

Figure 8:
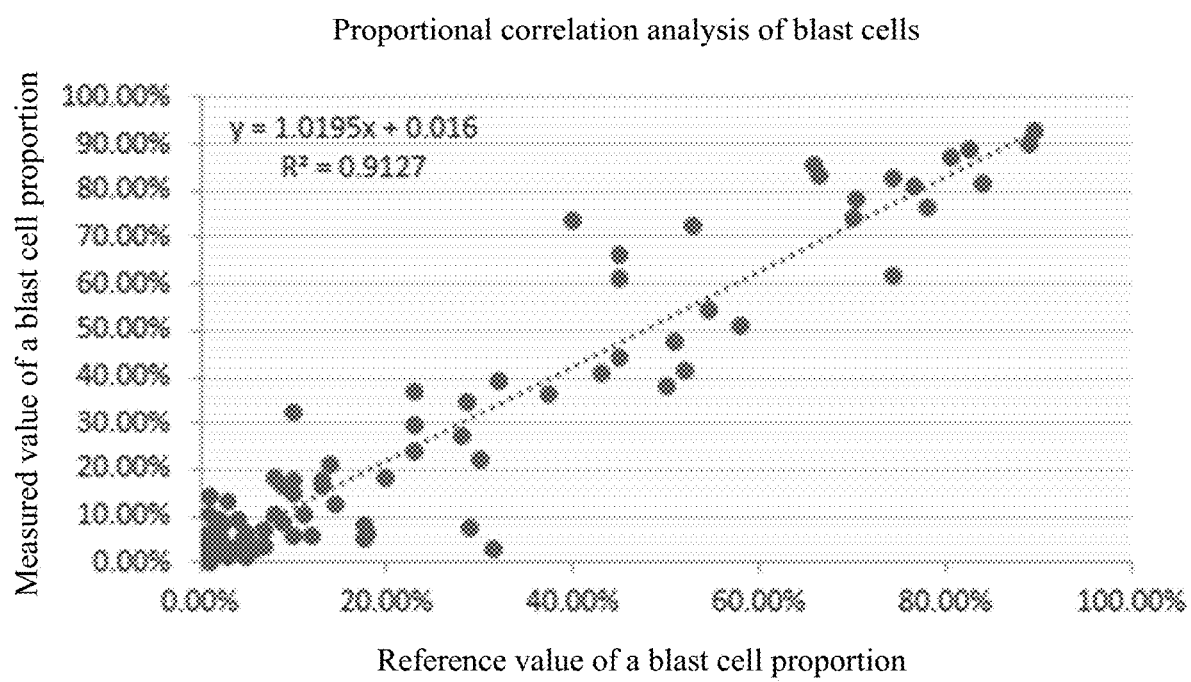
FIG. 8 is a comparison diagram of a blast cell parameter obtained by a sample analyzer according to an embodiment of the disclosure and a reference value of the blast cell parameter.

A result of comparative analysis of the measured value of the blast cell proportion and the reference value of the blast cell proportion is shown in FIG. 8. The blast cell proportion measured by the sample analyzer provided by the embodiments of the disclosure has a good correlation with the blast cell proportion obtained manually under the microscope, and the correlation coefficient reaches 0.95, that is, the sample analyzer provided by the embodiments of the disclosure can accurately measure the proportion of blast cells in blood samples.

The sample analyzer 100 according to the embodiments of the disclosure generates a scatter diagram based on side-scattered light signals and fluorescence signals, and can accurately obtain a blast cell parameter of a blood sample by analyzing a first predetermined feature region of the scatter diagram.

Figure 9:
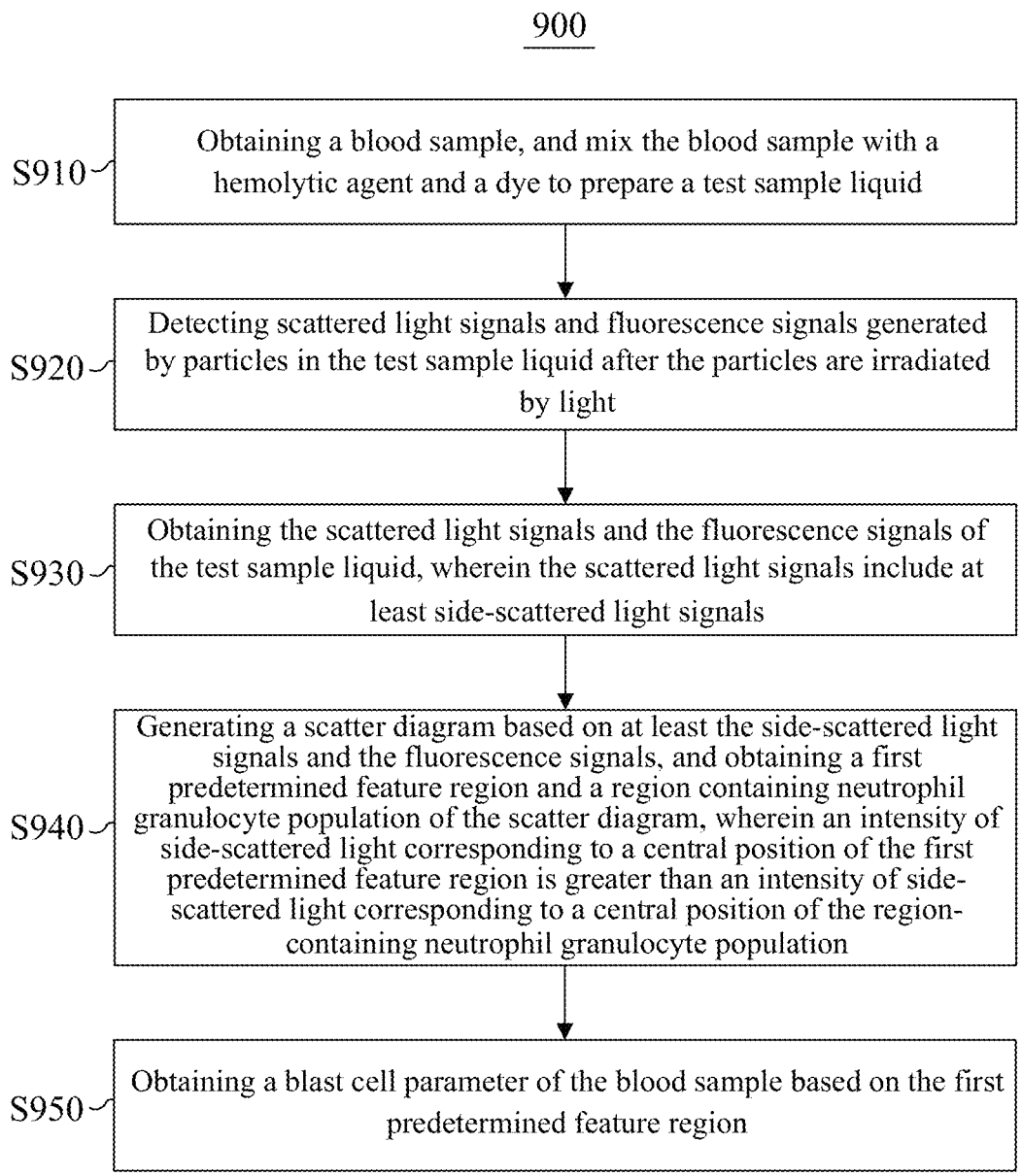
FIG. 9 is a schematic flowchart of a sample analysis method according to an embodiment of the disclosure.

Referring to FIG. 9, an embodiment of the disclosure further provides a sample analysis method 900, including the following steps:
at step S910, obtaining a blood sample, and mixing the blood sample with a hemolytic agent and a dye to prepare a test sample liquid;
at step S920, detecting scattered light signals and fluorescence signals generated by particles in the test sample liquid after the particles are irradiated by light;
at step S930, obtaining the scattered light signals and the fluorescence signals of the test sample liquid, where the scattered light signals include at least side-scattered light signals;
at step S940, generating a scatter diagram based on at least the side-scattered light signals and the fluorescence signals, and obtaining a first predetermined feature region and a region containing neutrophil granulocyte population of the scatter diagram; and
at step S950, obtaining a blast cell parameter of the blood sample based on the first predetermined feature region.

In an embodiment, a region of lymphocyte population of the scatter diagram is obtained, wherein an intensity of fluorescence corresponding to a central position of the first predetermined feature region is greater than an intensity of fluorescence corresponding to a central position of the region of lymphocyte population.

For example, the region containing neutrophil granulocyte population is a region of white blood cell population, and the region of white blood cell population includes a region of lymphocyte population and a region of neutrophil granulocyte population, eosinophil granulocyte population and monocyte population. The region containing neutrophil granulocyte population may also be a region of a separate neutrophil granulocyte population. The region containing neutrophil granulocyte population may also be a region of neutrophil granulocyte population, eosinophil granulocyte population and monocyte population.

In an embodiment, the blast cell parameter includes a particle concentration of blast cells, and the method further includes: generating alarm information when the particle concentration of the blast cells exceeds a first preset threshold. The blast cell parameter may further include a ratio of a particle concentration of blast cells to a particle concentration of white blood cells in the blood sample, and the method further includes: generating alarm information when the ratio exceeds a second preset threshold.

The particle concentration of the white blood cells in the blood sample may be obtained by at least one of the following manners: receiving the particle concentration of the white blood cells from externally input, obtaining the particle concentration of the white blood cells using other detection channels of the sample analyzer, and obtaining the particle concentration of the white blood cells based on the scattered light signals and/or the fluorescence signals.

In an embodiment, the scattered light signals further include forward-scattered light signals, and the method further includes: obtaining a nucleated red blood cell parameter and/or a basophil granulocyte parameter of the blood sample based on the forward-scattered light signals and the fluorescence signals.

Specifically, obtaining a nucleated red blood cell parameter and/or a basophil granulocyte parameter of the blood sample based on the forward-scattered light signals and the fluorescence signals includes: generating a two-dimensional scatter diagram based on the forward-scattered light signals and the fluorescence signals, and obtaining the nucleated red blood cell parameter and/or the basophil granulocyte parameter based on the two-dimensional scatter diagram; or, generating a three-dimensional scatter diagram based on the forward-scattered light signals, the side-scattered light signals and the fluorescence signals, obtaining the nucleated red blood cell parameter and/or the basophil granulocyte parameter according to the three-dimensional scatter diagram, and obtaining the blast cell parameter.

In an embodiment, the method further includes: obtaining a second predetermined feature region of the scatter diagram, wherein an intensity of side-scattered light corresponding to a central position of the second predetermined feature region is greater than the intensity of side-scattered light corresponding to the central position of the region containing neutrophil granulocyte population, and an intensity of fluorescence corresponding to the central position of the second predetermined feature region is greater than the intensity of fluorescence corresponding to the central position of the region of lymphocyte population; and obtaining an immature granulocyte parameter of the blood sample based on the second predetermined feature region.

The sample analysis method 900 according to the embodiments of the disclosure may be performed by the sample analyzer 100 described above. Those skilled in the art may understand the detailed process of the sample analysis method 900 according to the embodiments of the disclosure with reference to the foregoing description. For brevity, only some main operations are described herein, and for more details, reference may be made to the foregoing related description.

The sample analysis method 900 according to the embodiments of the disclosure generates a scatter diagram based on side-scattered light signals and fluorescence signals, and can accurately obtain a blast cell parameter of a blood sample by analyzing a first predetermined feature region of the scatter diagram.

Figure 10:
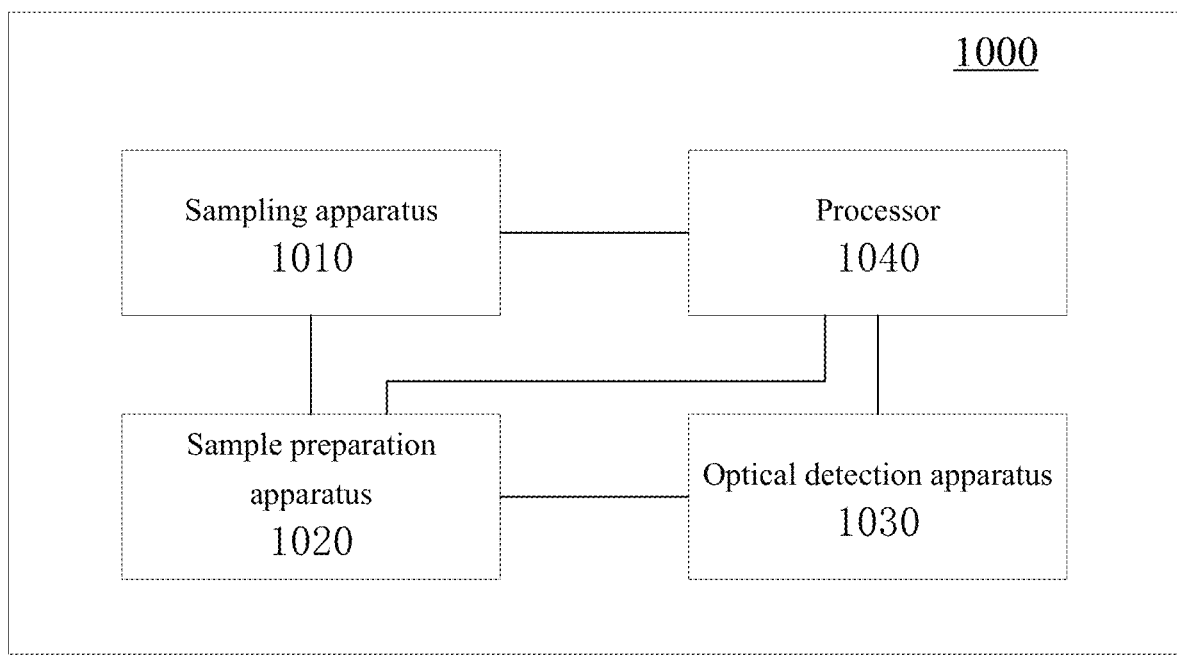
FIG. 10 is a structural block diagram of a sample analyzer according to another embodiment of the disclosure.

Another aspect of an embodiment of the disclosure provides a sample analyzer. Referring to FIG. 10, the sample analyzer 1000 includes a sampling apparatus 1010, a sample preparation apparatus 1020, an optical detection apparatus 1030, and a processor 1040. The sample analyzer 1000 according to this embodiment has a similar structure to the sample analyzer 100 described above. Only main functions of each component of the sample analyzer 1000 are described below. For more details, reference may be made to the related description of the sample analyzer 100 described above.

Specifically, the sampling apparatus 1010 is configured to collect a blood sample. The sample preparation apparatus 1020 is provided with a reaction chamber and a reagent supply portion, where the reaction chamber is configured to receive the blood sample collected by the sampling apparatus, and the reagent supply portion is configured to supply a hemolytic agent and a dye to the reaction chamber, so that the blood sample collected by the sampling apparatus is mixed with the hemolytic agent and the dye provided by the reagent supply portion in the reaction chamber to prepare a test sample liquid; wherein the hemolytic agent is used to lyse red blood cells, and the dye is used to stain organelles in blood cells. The optical detection apparatus 1030 includes a light source, a flow chamber and an optical detector, wherein the light source is configured to emit a light beam to irradiate the flow chamber, and the flow chamber is configured to communicate with the reaction chamber, wherein particles in the test sample liquid are capable of passing through the flow chamber one by one, and the optical detector is configured to detect, in a single test, scattered light signals and fluorescence signals generated by the particles passing through the flow chamber after the particles are irradiated by the light beam.

The processor 1040 is configured to perform the following steps: obtaining the scattered light signals and the fluorescence signals of the test sample liquid from the optical detection apparatus 1030, wherein the scattered light signals include forward-scattered light signals and side-scattered light signals; obtaining a blast cell parameter of the blood sample based on the side-scattered light signals and the fluorescence signals; and obtaining a nucleated red blood cell parameter and/or a basophil granulocyte parameter of the blood sample based on the forward-scattered light signals and the fluorescence signals.

Further, the sample analyzer 1000 may further include a display apparatus, configured to display a sample analysis result obtained by the processor 140.

Similar to the sample analyzer 100, the sample analyzer 1000 according to this embodiment also obtains a blast cell parameter of a blood sample based on fluorescence signals and side-scattered light signals. In addition, the sample analyzer 1000 further obtains a nucleated red blood cell parameter and/or a basophil granulocyte parameter of the blood sample based on the forward-scattered light signals and the fluorescence signals. The forward-scattered light signals, the side-scattered light signals and the fluorescence signals described above are optical signals obtained by using one test sample liquid in one same test. That is, the blast cell parameter, the nucleated red blood cell parameter and the basophil granulocyte parameter can be obtained simultaneously according to the optical signals obtained by using one test sample liquid in one same test.

In an embodiment, the sample analyzer 1000 may obtain a blast cell parameter by using the same method as the sample analyzer 100. Specifically, the processor 1040 generates a scatter diagram based on the side-scattered light signals and the fluorescence signals, and obtains a predetermined feature region and a region containing neutrophil granulocyte population of the scatter diagram. An intensity of side-scattered light corresponding to a central position of the predetermined feature region is greater than an intensity of side-scattered light corresponding to a central position of the region containing neutrophil granulocyte population. The processor 1040 may obtain the blast cell parameter of the blood sample based on the predetermined feature region. For a specific method for obtaining the blast cell parameter, reference may be made to the above description. Details are not described herein. For example, the processor 1040 may further generate alarm information when the blast cell parameter exceeds a preset threshold.

In an embodiment, the processor 1040 may generate different two-dimensional scatter diagrams, and obtain different cell parameters according to different two-dimensional scatter diagrams. Specifically, the processor 1040 may generate a first two-dimensional scatter diagram based on the side-scattered light signals and the fluorescence signals, and obtain the blast cell parameter based on the first two-dimensional scatter diagram; and generate a second two-dimensional scatter diagram based on the forward-scattered light signals and the fluorescence signals, and obtain at least one of the nucleated red blood cell parameter and the basophil granulocyte parameter based on the second two-dimensional scatter diagram. FIGS. 2 and 6 are an exemplary first two-dimensional scatter diagram and an exemplary second two-dimensional scatter diagram, respectively.

In another embodiment, the processor 1040 may generate a three-dimensional scatter diagram based on the forward-scattered light signals, the side-scattered light signals and the fluorescence signals, and obtain the nucleated red blood cell parameter, the basophil granulocyte parameter and the blast cell parameter according to the three-dimensional scatter diagram. Referring to FIG. 7, the processor 1040 may obtain the nucleated red blood cell parameter of the blood sample based on a region of nucleated red blood cell population in the three-dimensional scatter diagram, obtain the basophil granulocyte parameter of the blood sample based on a region of basophil granulocyte population in the three-dimensional scatter diagram, and obtain the blast cell parameter of the blood sample based on the first predetermined feature region in the three-dimensional scatter diagram.

In some embodiments, the processor 1040 may further obtain an immature granulocyte parameter of the blood sample in the same test while obtaining the blast cell parameter, the nucleated red blood cell parameter and the basophil granulocyte parameter. Specifically, the processor 1040 may obtain a predetermined feature region of the first two-dimensional scatter diagram corresponding to immature granulocytes, and obtain the immature granulocyte parameter of the blood sample based on the predetermined feature region corresponding to the immature granulocytes. For example, an intensity of side-scattered light corresponding to a central position of the predetermined feature region corresponding to the immature granulocytes is greater than the intensity of side-scattered light corresponding to the central position of the region containing neutrophil granulocyte population, and an intensity of fluorescence corresponding to the central position of the predetermined feature region corresponding to the immature granulocytes is greater than the intensity of fluorescence corresponding to the central position of the region of lymphocyte population.

Further, the sample analyzer 1000 may further obtain a classification and count of white blood cells based on optical signals obtained in the same test. A method for obtaining the classification and count of white blood cells may be the method based on a pulse width signal described above, but is not limited thereto. The processor 1040 may also generate a scatter diagram directly based on the optical signals, and obtain the classification and count of white blood cells based on the scatter diagram.

According to different pretreatment (such as different reagents) of a blood sample, the sample analyzer may divide the detection process of the blood sample into different detection channels, such as a white blood cell classification (DIFF) channel, a basophil granulocyte (BASO) channel, a nucleated red blood cell (NRBC) channel, and the like. The sample analyzer 1000 according to the embodiments of the disclosure may detect a blast cell parameter through a WNB (white blood cells, basophil granulocytes and nucleated red blood cells) channel, and obtain a blast cell parameter, a basophil granulocyte parameter, a nucleated red blood cell parameter and a white blood cell parameter in one single test.

The sample analyzer 1000 according to the embodiments of the disclosure may obtain a blast cell parameter and also obtain a nucleated red blood cell parameter and/or a basophil granulocyte parameter of a blood sample at the same time.

Figure 11:
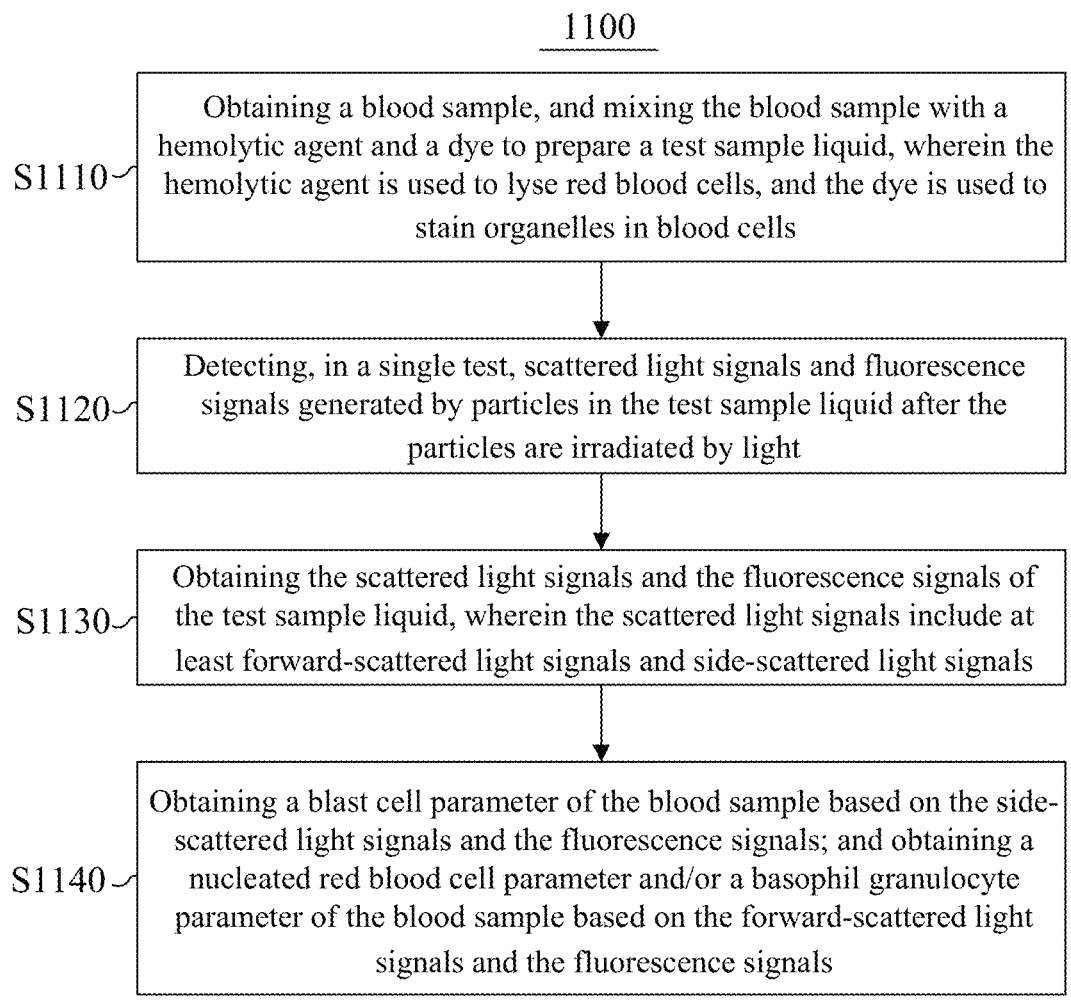
FIG. 11 is a schematic flowchart of a sample analysis method according to another embodiment of the disclosure.

Referring to FIG. 11, an embodiment of the disclosure further provides a sample analysis method 1100, including the following steps:

at step S1110, obtaining a blood sample, and mixing the blood sample with a hemolytic agent and a dye to prepare a test sample liquid, wherein the hemolytic agent is used to lyse red blood cells, and the dye is used to stain organelles in blood cells;

at step S1120, detecting, in a single test, scattered light signals and fluorescence signals generated by particles in the test sample liquid after the particles are irradiated by light;

at step S1130, obtaining the scattered light signals and the fluorescence signals of the test sample liquid, wherein the scattered light signals include at least forward-scattered light signals and side-scattered light signals;

at step S1140, obtaining a blast cell parameter of the blood sample based on the side-scattered light signals and the fluorescence signals; and step S1150: obtaining a nucleated red blood cell parameter and/or a basophil granulocyte parameter of the blood sample based on the forward-scattered light signals and the fluorescence signals.

The sample analysis method 1100 according to the embodiment of the disclosure may be performed by the sample analyzer 1000 described above. Those skilled in the art may understand the detailed process of the sample analysis method 1100 according to the embodiments of the disclosure with reference to the foregoing description. For brevity, only some main operations are described herein, and for more details, reference may be made to the foregoing related description.

In an embodiment, obtaining a blast cell parameter of the blood sample based on the side-scattered light signals and the fluorescence signals includes: generating a scatter diagram based on the side-scattered light signals and the fluorescence signals; obtaining a predetermined feature region and a region containing neutrophil granulocyte population of the scatter diagram, wherein an intensity of side-scattered light corresponding to a central position of the predetermined feature region is greater than an intensity of side-scattered light corresponding to a central position of the region containing neutrophil granulocyte population; and obtaining a blast cell parameter of the blood sample based on the predetermined feature region.

In an embodiment, obtaining a blast cell parameter of the blood sample based on the side-scattered light signals and the fluorescence signals includes: generating a first two-dimensional scatter diagram based on the side-scattered light signals and the fluorescence signals, and obtaining the blast cell parameter based on the first two-dimensional scatter diagram; and obtaining a nucleated red blood cell parameter and/or a basophil granulocyte parameter of the blood sample based on the forward-scattered light signals and the fluorescence signals includes: generating a second two-dimensional scatter diagram based on the forward-scattered light signals and the fluorescence signals, and obtaining the nucleated red blood cell parameter and/or the basophil granulocyte parameter based on the second two-dimensional scatter diagram.

In an embodiment, obtaining a blast cell parameter of the blood sample based on the side-scattered light signals and the fluorescence signals; and obtaining a nucleated red blood cell parameter and/or a basophil granulocyte parameter of the blood sample based on the forward-scattered light signals and the fluorescence signals include: generating a three-dimensional scatter diagram based on the forward-scattered light signals, the side-scattered light signals and the fluorescence signals, obtaining the nucleated red blood cell parameter and/or the basophil granulocyte parameter, and the blast cell parameter according to the three-dimensional scatter diagram.

The sample analysis method 1100 according to the embodiment of the disclosure can be used to obtain the blast cell parameter and also obtain the nucleated red blood cell parameter and/or the basophil granulocyte parameter of the blood sample at the same time.

Although the exemplary embodiments have been described here with reference to the accompanying drawings, it should be understood that the exemplary embodiments described above are merely exemplary, and are not intended to limit the scope of the disclosure thereto. Those of ordinary skill in the art may make various changes and modifications therein without departing from the scope and spirit of the disclosure. All such changes and modifications are intended to be included in the scope of the disclosure as claimed in the appended claims.

Those of ordinary skill in the art would have appreciated that the units and algorithm steps of the examples described in conjunction with the embodiments disclosed herein may be implemented in electronic hardware or a combination of computer software and electronic hardware. Whether the functions are performed by hardware or software depends on particular applications and design constraint conditions of the technical solutions. Those skilled in the art could use different methods to implement the described functions for each particular application, but such implementation should not be considered to be beyond the scope of the disclosure.

In several embodiments provided in the disclosure, it should be understood that the disclosed devices and methods may be implemented in other ways. For example, the device embodiments described above are merely exemplary. For example, the division of units is merely a logical function division. In actual implementations, there may be other division methods. For example, a plurality of units or assemblies may be combined or integrated into another device, or some features may be omitted or not implemented.

A large number of specific details are explained in this description provided herein. However, it could be understood that the embodiments of the disclosure can be practiced without these specific details. In some instances, well-known methods, structures, and technologies are not shown in detail, so as not to obscure the understanding of this description.

Similarly, it should be understood that in order to simplify the disclosure and help to understand one or more of various aspects of the disclosure, in the description of the exemplary embodiments of the disclosure, various features of the disclosure are sometimes together grouped into an individual embodiment, figure or description thereof. However, the method of the disclosure should not be construed as reflecting the following intention: namely, the disclosure set forth requires more features than those explicitly stated in each claim. More precisely, as reflected by the corresponding claims, the inventive point thereof lies in that features that are fewer than all the features of an individual embodiment disclosed may be used to solve the corresponding technical problem. Therefore, the claims in accordance with the particular embodiments are thereby explicitly incorporated into the particular embodiments, where each claim itself serves as an individual embodiment of the disclosure.

Those skilled in the art should understand that, unless the features are mutually exclusive, any combination may be used to combine all the features disclosed in this description (along with the appended claims, abstract, and drawings) and all the processes or units of any of methods or devices as disclosed. Unless explicitly stated otherwise, each feature disclosed in this description (along with the appended claims, abstract, and drawings) may be replaced by an alternative feature that provides the same, equivalent, or similar objective.

In addition, those skilled in the art should understand that although some of the embodiments described herein include some but not other features included in other embodiments, combinations of features of different embodiments are meant to be within the scope of the disclosure, and form different embodiments. For example, in the claims, any one of the embodiments set forth thereby can be used in any combination.

Various embodiments regarding components in the disclosure may be implemented in hardware, or implemented by software modules running on one or more processors, or implemented in a combination thereof. It should be understood for those skilled in the art that a microprocessor or a digital signal processor (DSP) may be used in practice to implement some or all of the functions of some modules in an article analysis device according to an embodiment of the disclosure. The disclosure may further be implemented as an apparatus program (e.g., a computer program and a computer program product) for executing some or all of the methods described herein. Such a program for implementing the disclosure may be stored on a computer-readable medium, or may be in the form of one or more signals. Such a signal may be downloaded from an Internet website, or provided on a carrier signal, or provided in any other form.

It should be noted that the description of the disclosure made in the above-mentioned embodiments is not to limit the disclosure, and those skilled in the art may design alternative embodiments without departing from the scope of the appended claims. In the claims, any reference signs placed between parentheses should not be construed as limitation on the claims. The term "including" does not exclude the presence of elements or steps not listed in the claims. The term "a" or "an" preceding an element does not exclude the presence of a plurality of such elements. The disclosure may be implemented by means of hardware including several different elements and by means of an appropriately programmed computer. In unit claims listing several apparatuses, several of these apparatuses may be specifically embodied by one and the same item of hardware. The use of the terms "first", "second", "third", etc. does not indicate any order. These terms may be interpreted as names.

The above descriptions are merely the specific embodiments of the disclosure or the description of the specific embodiments, but the scope of protection of the disclosure is not limited thereto. Any changes or substitutions readily conceivable by those skilled in the art within the technical scope disclosed in the disclosure shall fall within the scope of protection of the disclosure. Therefore, the scope of protection of the disclosure should be subject to the scope of protection of the claims.

What is claimed is:

1. A sample analyzer, comprising:
a sampling apparatus configured to collect a blood sample;
a sample preparation apparatus provided with a reaction chamber and a reagent supply portion, wherein the reaction chamber is configured to receive the blood sample collected by the sampling apparatus, and the reagent supply portion is configured to supply a hemolytic agent and a dye to the reaction chamber, so that the blood sample collected by the sampling apparatus is mixed with the hemolytic agent and the dye provided by the reagent supply portion in the reaction chamber to prepare a test sample liquid, and wherein the hemolytic agent is used to lyse red blood cells, and the dye is used to stain organelles in blood cells;
an optical detection apparatus comprising a light source, a flow chamber and an optical detector, wherein the light source is configured to emit a light beam to irradiate the flow chamber, the flow chamber is configured to communicate with the reaction chamber, wherein particles in the test sample liquid are capable of passing through the flow chamber one by one, and the optical detector is configured to detect, in a single test, scattered light signals and fluorescence signals generated by the particles passing through the flow chamber after the particles are irradiated by the light beam; and
a processor configured to perform the following steps:
obtaining the scattered light signals and the fluorescence signals of the test sample liquid detected by the optical detection apparatus in the single test of the test sample liquid, wherein the scattered light signals comprise forward-scattered light signals and side-scattered light signals;
obtaining a particle concentration of blast cells in the blood sample based on the side-scattered light signals and the fluorescence signals; and obtaining a particle concentration of nucleated red blood cells and/or a particle concentration of basophil granulocytes in the blood sample based on the forward-scattered light signals and the fluorescence signals, so as to obtain the particle concentration of blast cells and the particle concentration of nucleated red blood cells and/or the particle concentration of basophil granulocytes in the single test.

2. The sample analyzer of claim 1, wherein obtaining a particle concentration of blast cells in the blood sample based on the side-scattered light signals and the fluorescence signals comprises:
generating a scatter diagram based on the side-scattered light signals and the fluorescence signals;
obtaining a first predetermined feature region of the scatter diagram, wherein an intensity of side-scattered light corresponding to a central position of the predetermined feature region is greater than an intensity of side-scattered light corresponding to a central position of a region containing neutrophil granulocyte population of the scatter diagram; and
obtaining the particle concentration of blast cells in the blood sample based on the predetermined feature region.

3. The sample analyzer of claim 2, wherein an intensity of fluorescence corresponding to the central position of the first predetermined feature region is greater than an intensity of fluorescence corresponding to a central position of a region of lymphocyte population of the scatter diagram.

4. The sample analyzer of claim 3, wherein the processor is further configured to perform the following steps:
obtaining a second predetermined feature region of the scatter diagram, wherein an intensity of side-scattered light corresponding to a central position of the second predetermined feature region is greater than the intensity of side-scattered light corresponding to the central position of the region containing neutrophil granulocyte population, and an intensity of fluorescence corresponding to the central position of the second predetermined feature region is greater than the intensity of fluorescence corresponding to the central position of the region of lymphocyte population; and
obtaining an immature granulocyte parameter of the blood sample based on the second predetermined feature region.

5. The sample analyzer of claim 1, wherein the region containing neutrophil granulocyte population is a region of white blood cell population, and the region of white blood cell population contains a region of lymphocyte population and a region of neutrophil granulocyte population, eosinophil granulocyte population and monocyte population; or
wherein the region containing neutrophil granulocyte population is a region of neutrophil granulocyte population; or
wherein the region containing neutrophil granulocyte population is a region of neutrophil granulocyte population, eosinophil granulocyte population and monocyte population.

6. The sample analyzer of claim 1, wherein the processor is further configured to generate alarm information when the particle concentration of the blast cells exceeds a first preset threshold.

7. The sample analyzer of claim 1, wherein the processor is further configured to calculate a ratio of the particle concentration of blast cells to a particle concentration of white blood cells in the blood sample and generate alarm information when the ratio exceeds a second preset threshold.

8. The sample analyzer of claim 7, wherein the processor is further configured to obtain the particle concentration of the white blood cells in the blood sample by at least one of the following manners:
receiving the particle concentration of the white blood cells from external input;

obtaining the particle concentration of the white blood cells using other detection channels; and obtaining the particle concentration of the white blood cells based on the scattered light signals and/or the fluorescence signals.

9. The sample analyzer of claim 1, wherein obtaining a particle concentration of blast cells in the blood sample based on the side-scattered light signals and the fluorescence signals comprises: generating a first two-dimensional scatter diagram based on the side-scattered light signals and the fluorescence signals, and obtaining the particle concentration of blast cells based on the first two-dimensional scatter diagram; and obtaining a particle concentration of nucleated red blood cells and/or a particle concentration of basophil granulocytes in the blood sample based on the forward-scattered light signals and the fluorescence signals comprises: generating a second two-dimensional scatter diagram based on the forward-scattered light signals and the fluorescence signals, and obtaining the particle concentration of nucleated red blood cells and/or the particle concentration of basophil granulocytes based on the second two-dimensional scatter diagram.

10. The sample analyzer of claim 1, wherein obtaining a particle concentration of blast cells in the blood sample based on the side-scattered light signals and the fluorescence signals; and obtaining a particle concentration of nucleated red blood cells and/or a particle concentration of basophil granulocytes in the blood sample based on the forward-scattered light signals and the fluorescence signals comprise:

generating a three-dimensional scatter diagram based on the forward-scattered light signals, the side-scattered light signals and the fluorescence signals, obtaining the particle concentration of nucleated red blood cells and/or the particle concentration of basophil granulocytes and the particle concentration of blast cells according to the three-dimensional scatter diagram.

11. A sample analyzer, comprising:

a sampling apparatus configured to collect a blood sample;

a sample preparation apparatus provided with a reaction chamber and a reagent supply portion, wherein the reaction chamber is configured to receive the blood sample collected by the sampling apparatus, and the reagent supply portion is configured to supply a hemolytic agent and a dye to the reaction chamber, so that the blood sample collected by the sampling apparatus is mixed with the hemolytic agent and the dye provided by the reagent supply portion in the reaction chamber to prepare a test sample liquid;

an optical detection apparatus comprising a light source, a flow chamber and an optical detector, wherein the light source is configured to emit a light beam to irradiate the flow chamber, the flow chamber is configured to communicate with the reaction chamber, wherein particles in the test sample liquid are capable of passing through the flow chamber one by one, and the optical detector is configured to detect scattered light signals and fluorescence signals generated by the particles passing through the flow chamber after the particles are irradiated by the light beam; and a processor configured to perform the following steps:
obtaining the scattered light signals and the fluorescence signals of the test sample liquid from the optical detection apparatus, wherein the scattered light signals comprise at least side-scattered light signals;

generating a scatter diagram based on at least the side-scattered light signals and the fluorescence signals, and obtaining a first predetermined feature region of the scatter diagram, wherein an intensity of side-scattered light corresponding to a central position of the first predetermined feature region is greater than an intensity of side-scattered light corresponding to a central position of a region containing neutrophil granulocytes population of the scatter diagram; and obtaining a particle concentration of blast cells in the blood sample based on the first predetermined feature region.

12. The sample analyzer of claim 11, wherein an intensity of fluorescence corresponding to the central position of the first predetermined feature region is greater than an intensity of fluorescence corresponding to a central position of a region of lymphocyte population of the scatter diagram.

13. The sample analyzer of claim 12, wherein the processor is further configured to perform the following steps:

obtaining a second predetermined feature region of the scatter diagram, wherein an intensity of side-scattered light corresponding to a central position of the second predetermined feature region is greater than the intensity of side-scattered light corresponding to the central position of the region containing neutrophil granulocyte population, and an intensity of fluorescence corresponding to the central position of the second predetermined feature region is greater than the intensity of fluorescence corresponding to the central position of the region of lymphocyte population; and obtaining an immature granulocyte parameter of the blood sample based on the second predetermined feature region.

14. The sample analyzer of claim 11, wherein the scattered light signals further comprise forward-scattered light signals, and the processor is further configured to perform the following step:

obtaining a particle concentration of nucleated red blood cells and/or a particle concentration of basophil granulocytes in the blood sample based on the forward-scattered light signals and the fluorescence signals.

15. The sample analyzer of claim 14, wherein obtaining a particle concentration of nucleated red blood cells and/or a particle concentration of basophil granulocytes in the blood sample based on the forward-scattered light signals and the fluorescence signals comprises:

generating a two-dimensional scatter diagram based on the forward-scattered light signals and the fluorescence signals, and obtaining the particle concentration of nucleated red blood cells and/or the particle concentration of basophil granulocytes based on the two-dimensional scatter diagram; or, generating a three-dimensional scatter diagram based on the forward-scattered light signals, the side-scattered light signals and the fluorescence signals, obtaining the particle concentration of nucleated red blood cells and/or the particle concentration of basophil granulocytes and the particle concentration of blast cells according to the three-dimensional scatter diagram.

* * * * *